United States Patent [19]

Jonson

[11] 4,022,200
[45] May 10, 1977

[54] MEDICAL FACIAL MASK

[75] Inventor: Bjorn Jonson, Lund, Sweden

[73] Assignee: Siemens Aktiengesellschaft, Berlin & Munich, Germany

[22] Filed: Sept. 8, 1975

[21] Appl. No.: 611,392

Related U.S. Application Data

[63] Continuation of Ser. No. 474,683, May 30, 1974, abandoned.

[52] U.S. Cl. .................... 128/141 R; 128/204; 128/146.7
[51] Int. Cl.[2] ........................ A61M 16/00
[58] Field of Search .......... 128/141 R, 146, 146.7, 128/142, 142.3, 142.4, 142.7, 140 R, 145 R, 145.5, 145.8, 203, 204, 298, 299, 185, 191 R, 191 A, 195, 30, 30.2, 1 B

[56] References Cited

UNITED STATES PATENTS

| | | | |
|---|---|---|---|
| 2,749,910 | 6/1956 | Faulconer, Jr. | 128/30.2 |
| 2,877,764 | 3/1959 | Galleher, Jr. | 128/146 |
| 3,552,391 | 1/1971 | Deaton | 128/203 |
| 3,786,809 | 1/1974 | Kitrilakis | 128/191 A |

FOREIGN PATENTS OR APPLICATIONS

| | | | |
|---|---|---|---|
| 18,871 | 8/1912 | United Kingdom | 128/141 |

*Primary Examiner*—Robert W. Michell
*Assistant Examiner*—Henry J. Recla
*Attorney, Agent, or Firm*—Hill, Gross, Simpson, Van Santen, Steadman, Chiara & Simpson

[57] ABSTRACT

A facial mask for the transmission of a gaseous medium to a patient, which incorporates a sealing arrangement which is not damaging to the skin and, concurrently, hermetically seals off the face of the patient. The rim of a facial mask which is adapted to be positioned against the head of the patient has a sealing part which consists of such a material so as to be placeable into a rigid condition through the intermediary of a vacuum or reduced pressure which is present in the sealing part. A removable lid may be provided on the facial mask thereby facilitating that, if need be, the physician is capable of simple and rapid exposure of the patient's face.

6 Claims, 1 Drawing Figure

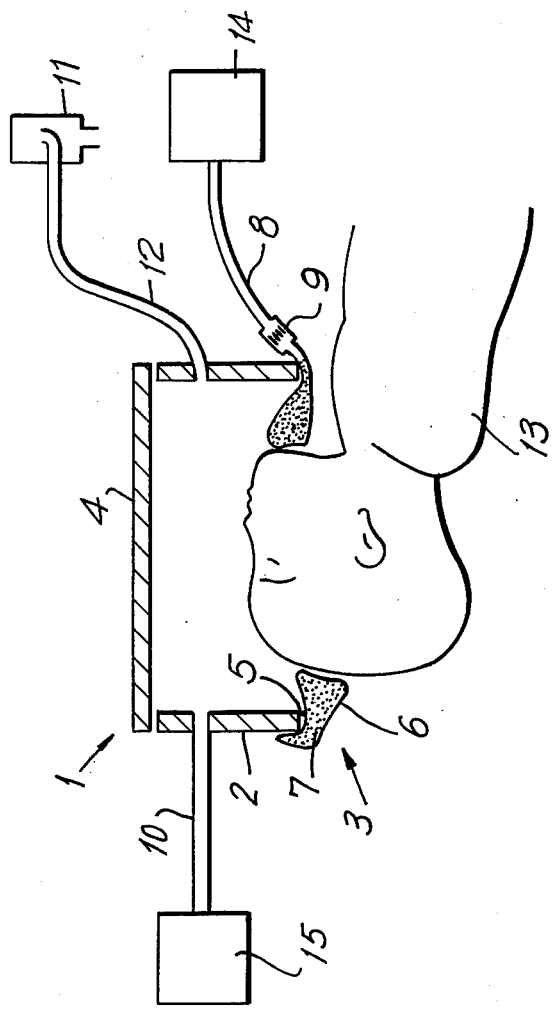

MEDICAL FACIAL MASK

This application is a continuation application of Ser. No. 474,683, filed May 30, 1974 now abandoned.

FIELD OF THE INVENTION

The present invention relates to a facial mask for the transmission of a gaseous medium to a patient.

DISCUSSION OF THE PRIOR ART

In known masks of this type, it is extremely difficult to obtain a sufficient degree of sealing without the need for adhesive strips, adhesive materials, and the application of a strong pressure against the skin. The sealings of the known masks are subject to the disadvantage in causing irritation or injury to the tissues of the skin. Other known facial masks are closely sealed about the mouth and nose, or about the throat, and thereby effect a compression of skin zones which are psychologically and physiologically sensitive. Furthermore, in the use of heretofore known facial masks, the extent of exposure and accessibility to the face and air breathing passages necessary for treatment is extremely limited.

SUMMARY OF THE INVENTION

Accordingly, it is an object of the present invention to provide a facial mask of the above-mentioned type, which incorporates a sealing arrangement which is not damaging to the skin and, concurrently, hermetically seals off the face of the patient.

The foregoing object is inventively attained in that the rim of a facial mask adapted to be positioned against the head of a patient has a sealing part which consists of such a material so as to be placeable into a rigid condition through the intermediary of a vacuum or reduced pressure which is present in the sealing part. In an advantageous embodiment of the invention it is contemplated to sealingly provide a removable lid on the facial mask. This facilitates that, if need be, the physician is capable of affording simple and rapid exposure of the patient's face.

BRIEF DESCRIPTION OF THE DRAWING

Further advantages and details of the invention may be ascertained from the single FIGURE of the drawing showing an exemplary embodiment of a facial mask constructed in accordance with the invention.

DETAILED DESCRIPTION

Referring now in detail to the drawing, the latter illustrates a facial mask 1 which encloses the face of a supine patient 13 and, namely, on both sides of the scalp, ahead of the ears, and below the chin. The mask 1 encompasses a rigid hollow cylinder 2, and a sealing part 3 located at the rim thereof which extends toward the face, as well as a rigid removable lid 4 at the upper rim of the cylinder. The cylinder 2 and the lid 4 each consist of a transparent plastic material, so that the face of the patient 13 is fully visible to the physician. When needed, the lid 4 may be removed so as to expose the face. At the lower end surface of the cylinder 2, the sealing part 3 is securely fastened thereto in an air-tight manner. The sealing part 3 consists of a jacket 6 which is formed of a soft and possibly elastic material which air-tightly contacts the face, for example, a thin latex sheet, and the interior of which is filled with a powder material 7 constituted of, for example, small plastic material particles. With the aide of a suction device 14, the air may be evacuated from the sealing part 3 through a conduit 8 communicating with the interior of jacket 6. A filter 9 is located in the conduit 8 so as to prevent the plastic material particles from being aspirated out during the air evacuation sequence. At a reduced pressure interiorly of part 3, the latter stiffens, maintains the sealing about the face of the patient 13, and positions the sealing due to its stiffness.

From a receptacle 15, inhalating gases are introduced into the facial mask 1 through a connecting conduit 10. This may be in the form of a continuous gas flow, and be effected with a pressure which only minutely differs from atmospheric pressure. The inhalating gas may have a predetermined composition, for example, for oxygen therapy such as oxygen, oxygen-enriched air, and/or anesthesia, or by means of analysis of the composition of the gases upon leaving the facial mask as a result of the material changes in the body, provide information through the gas transformation.

The gas infeed may be so controlled, that a continual excess pressure is present in the facial mask 1. The gas flows from the mask 1 by means of a conduit 12 through a pressure regulating valve 11. In this embodiment, the facial mask is particularly suitable for the treatment of infants.

The infeed of gas to the facial mask may also be carried out whereby an intermittent excess pressure is obtained in the mask. This is rendered possible when a respirator is connected to conduits 10 and 12. In that instance, the treatment assumes the character of a respirator treatment program.

While there has been shown what is considered to be the preferred embodiment of the invention, it will be obvious that modifications may be made which come within the scope of the disclosure of the specification.

What is claimed is:

1. Medical facial mask for use with a patient lying in a supine position, said mask having an aperture; a source of gaseous medium; conduit means connecting said source to said aperture for transmitting the gaseous medium to a patient wearing said mask, said mask including a hollow transparent cylindrical portion having a uniform interior diameter defining said aperture and having a first end surface thereof of a size sufficient to extend over and encompass the face of the patient, a removable transparent lid portion being fastened to the opposite end surface of said cylindrical mask portion, sealing means tightly fastened to said first end surface of said mask along the circumference thereof and extending radially inwardly thereof towards the face of the patient, said sealing means including a hollow ring member formed of a generally soft elastic material, and a powder material filling the interior of said ring member; aspirating means; and suction conduit means extending laterally from said cylindrical portion and connecting said aspirating means to the interior of said ring member whereby, upon evacuating the air from the interior of said ring member, said sealing means is brought into a stiffened condition so as to hermetically seal the face of the patient within said facial mask; said conduit means also extending laterally from said cylindrical portion whereby, accessibility and visibility to said patient is attained.

2. Facial mask as claimed in claim 1, comprising means communicating with the interior of said mask for maintaining an increased pressure in said mask and in the air breathing passages of the patient wearing the mask.

3. Facial mask as claimed in claim 2, said means communicating with the interior of said mask comprising a conduit and a pressure regulating valve connected to said conduit to continually convey said gaseous medium into said mask.

4. Facial mask as claimed in claim 1, comprising means for generating an intermittent excess pressure in the space between the face of the patient and the inner surface of said mask.

5. Facial mask as claimed in claim 1, said gaseous medium having a predetermined composition, the gas emanating from said mask adapted to be analyzed for determining the consumption of gas in the body of the patient.

6. Facial mask as claimed in claim 1, said conduit means communicating with the interior of said hollow ring member for evacuating air therefrom including filter means positioned therein for preventing egress of said powder material from said member.

* * * * *